United States Patent [19]

Olsson

[11] Patent Number: 5,565,566
[45] Date of Patent: * Oct. 15, 1996

[54] N⁶-SUBSTITUTED 9-METHYLADENINES: A NEW CLASS OF ADENOSINE RECEPTOR ANTAGONISTS

[75] Inventor: Ray A. Olsson, Tampa, Fla.

[73] Assignee: Discovery Therapeutics, Inc., Richmond, Va.

[ * ] Notice: The portion of the term of this patent subsequent to Nov. 19, 2008, has been disclaimed.

[21] Appl. No.: 378,285

[22] Filed: Jan. 26, 1995

Related U.S. Application Data

[63] Continuation of Ser. No. 73,916, Jun. 8, 1993, abandoned, which is a continuation-in-part of Ser. No. 304,346, Jan. 31, 1981, abandoned, which is a continuation-in-part of Ser. No. 42,383, Apr. 24, 1987, abandoned.

[51] Int. Cl.⁶ .......................... C07D 473/34; A61K 31/52
[52] U.S. Cl. ................................................ 544/277
[58] Field of Search ............................................. 544/277

[56] References Cited

U.S. PATENT DOCUMENTS

| | | | |
|---|---|---|---|
| 2,881,164 | 4/1959 | Kissman et al. | 260/211.5 |
| 3,502,649 | 3/1970 | Thiel et al. | 260/211.5 |
| 3,509,129 | 4/1970 | Kampe et al. | 260/211.5 |
| 3,796,700 | 3/1974 | Yoshioka et al. | 260/211.5 |
| 3,851,056 | 11/1974 | Stork et al. | 424/180 |
| 3,901,876 | 8/1975 | Vorbrüggen et al. | 260/211.5 |
| 3,929,763 | 12/1975 | Fauland et al. | 260/211.5 |
| 3,930,005 | 12/1975 | Wojnar et al. | 424/253 |
| 3,989,833 | 11/1976 | Jonas et al. | 424/253 |
| 4,029,884 | 6/1977 | Stein et al. | 536/26 |
| 4,081,534 | 3/1978 | Elion et al. | 424/180 |
| 4,090,021 | 5/1978 | Vorbruggen | 536/28 |
| 4,167,565 | 9/1978 | Stein et al. | 424/180 |
| 4,189,485 | 2/1980 | Matsuno et al. | 424/253 |
| 4,199,574 | 4/1980 | Schaeffer | 424/200 |
| 4,224,438 | 9/1980 | Fauland et al. | 536/26 |
| 4,287,188 | 9/1981 | Schaeffer | 424/200 |
| 4,294,831 | 10/1981 | Schaeffer | 424/253 |
| 4,364,922 | 12/1982 | Berne et al. | 424/9 |
| 4,440,777 | 4/1984 | Zupan | 424/274 |
| 4,495,180 | 1/1985 | Alexander | 514/46 |
| 4,514,405 | 4/1985 | Irmscher et al. | 514/46 |
| 4,612,315 | 9/1986 | Jacobson et al. | 514/263 |
| 4,696,932 | 9/1987 | Jacobson et al. | 514/263 |
| 4,714,697 | 12/1987 | Trivedi | 514/46 |
| 4,751,292 | 6/1988 | Fox | 536/24 |
| 4,783,530 | 11/1988 | Rzeszotarski et al. | 544/267 |
| 4,798,833 | 1/1989 | Johansson et al. | 514/262 |
| 4,853,386 | 8/1989 | Friebe et al. | 514/266 |
| 4,980,379 | 12/1990 | Belardinelli et al. | 514/821 |
| 5,066,655 | 11/1991 | Olsson | 514/261 |
| 5,117,830 | 6/1992 | McAfee | 128/654 |
| 5,256,398 | 10/1993 | McAfee | 424/9 |

FOREIGN PATENT DOCUMENTS 657337  2/1963  Canada .

| | | |
|---|---|---|
| 0155911 | 9/1985 | European Pat. Off. . |
| 0497258 | 8/1992 | European Pat. Off. . |
| 0503563 | 9/1992 | European Pat. Off. . |
| 0501379 | 9/1992 | European Pat. Off. . |

(List continued on next page.)

OTHER PUBLICATIONS

"New Ways to Scan the Myocardium," *The Medical Letter* 33:87–90 (1991).

Bertolet et al., "Attenuation of Adenosine–Induced Chest Pain with N–0861 (N⁶–Endonorbornan–2–yl–9–methyladenine), A Selective A₁ Adenosine Receptor Antagonist," *5th Amer. Coll. of Cardiol., 43rd Annual Sci. Session* (Mar. 1994).

(List continued on next page.)

*Primary Examiner*—Mark L. Berch
*Attorney, Agent, or Firm*—Sterne, Kessler, Goldstein & Fox, P.L.L.C.

[57]  ABSTRACT

Novel compounds and a method of using them to antagonize adenosine receptors are provided wherein the compounds are selected from the group of racemic mixtures or optically active compounds represented by the general formula:

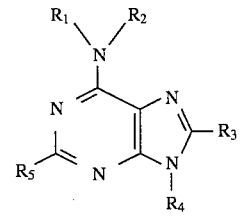

wherein $R_2$ is selected from the group consisting of cycloalkyl radicals having from 3 to 8, preferably 3 to 7, ring carbon atoms, alkyl radicals having from 1 to 10, carbon atoms, aralkyl radicals having from 7 to 14, preferably 7 to 10, carbon atoms, and heteroatom- and halogen-substituted derivatives thereof wherein said heteroatom may be selected from the group consisting of nitrogen, phosphorus, sulfur and oxygen; $R_1$ may be hydrogen or $R_2$, and $R_3$ is selected from the group consisting of hydrogen, halogen, amine, carboxy, thio, sufonate, sulfonamide, sulfone, sulfoxamide, phenyl, alkyl-substituted amine, cycloalkyl-substituted amine, alkyl radicals having from 1 to 10 carbon atoms, and cycloalkyl radicals having from 3 to 8, preferably 5 to 6, ring carbon atoms. $R_4$ is selected from the group consisting of benzyl, phenyl, and alkyl groups comprising from 1 to 4 carbon atoms, wherein said alkyl group can be substituted with oxygen, for example ethers and alcohols. $R_5$ is selected from the group consisting of hydrogen; hydroxy; sulfonate; halogen; alkoxy and cycloalkoxy groups comprising 1 to 6 carbon atoms, wherein said alkoxy and cycloalkoxy groups can be substituted with phenyl; and amine, wherein said amine can be substituted with alkyl, cycloalkyl, or phenyl. Optically active compounds are especially active as antagonists of $A_1$ adenosine receptors.

2 Claims, No Drawings

FOREIGN PATENT DOCUMENTS

| | | |
|---|---|---|
| 2081524 | 12/1971 | France . |
| 2195434 | 3/1974 | France . |
| 3529497 | 12/1987 | Germany . |
| 47-45758 | 11/1972 | Japan . |
| 60-6616 | 1/1985 | Japan . |
| 4-346986 | 12/1992 | Japan . |
| 953897 | 4/1964 | United Kingdom . |
| 1123245 | 8/1968 | United Kingdom . |
| 2041359 | 9/1980 | United Kingdom . |
| 2077726 | 12/1981 | United Kingdom . |
| WO88/00192 | 1/1988 | WIPO . |
| WO88/08303 | 11/1988 | WIPO . |
| WO92/00297 | 1/1992 | WIPO . |

OTHER PUBLICATIONS

Jacobson et al., "Adenosine Receptors: Pharmacology, Structure–Activity Relationships, and Therapeutic Potential," *J. Med. Chem.* 35(3):407–422 (1992).

McNulty, S. A., "Pharmacological Interventional Testing for Myocardial Perfusion: A New Application for Adenosine," *Cardiovascular Nursing* 28(4):24–28 (1992).

Rose et al., "Safety, Tolerability, Renal Effects and Pharmacokinetics in Man of Single Doses of FK453, A Novel Adenosine $A_1$ Receptor Antagonist," Presented at the British Pharmacological Society Meeting, Abstract P149 (1991).

Stiles, G. L., "Adenosine Receptors: Structure, Function and Regulation," *TIPS Reviews:*486–490 (Dec. 1986).

Terai et al., "The renal effects of FR–113453, a potent non–xanthine adenosine antagonist," *XIth Intl. Cong. of Pharmacol.*, Amsterdam, The Netherlands, Abstract No. P.tu.435 (Jul. 2–6, 1990).

Translation of JP–58–167599.

Translation of JP–58 167800.

Anzai and Matsui, "Compounds relating to dibenzoyladenine riboside. Choice between the $N^6$,1–dibenzoyl and $N^6,N^6$–dibenzoyl structures," *Chem. Abstracts* 80(3):454 Abstract No. 15146c (1974).

Baer and Muller, "Adenosine receptors in smooth muscle," in: Regulatory Function of Adenosine, Berne et al., eds., Boston, p. 500 (1983).

Bruns, R. F., "Adenosine Antagonism by Purines, Pteridines and Benzopteridines in Human Fibroblasts," *Biochem. Pharmacol.* 30:325–333 (1981).

Bruns et al., "Characterization of the $A_2$ Adenosine Receptor Labeled by [$^3$H]NECA in Rat Striatal Membranes," *Molec. Pharmacol.* 29:331–346 (1986).

Burnstock et al., "Evidence that the $P_1$–purinoceptor in the guinea pig *taenia coli* is an $A_2$–subtype," *Br. J. Pharmacol.* 81:533–541 (1984).

Carstens and Goldner, "6,9–Disubstituted purine derivatives," *Chem. Abstracts* 56(9):Abstract No. 10167i–10168d (1962).

Collis, M. G., "Evidence for an $A_1$–adenosine receptor in the guinea pig atrium," *Br. J. Pharmacol.* 78:207–212 (1983).

Daly, J. W., "Adenosine Receptors," *Advances in Cyclic Nucleotide and Protein Phosphorylation Research* 19:29–46 (1985).

Daly, J. W., "Adenosine Receptors: Targets for Future Drugs," *J. Med. Chem.* 25(3):197–207 (1982).

Daly et al., "Non–xanthine heterocycles: activity as antagonists of $A_1$– and $A_2$–adenosine receptors," *Chem. Abstracts* 108(21):Abstract No. 179589x (1988).

Daly et al., "Structure–Activity Relationship for $N^6$–Substituted Adenosines at a Brain $A_1$–Adenosine Receptor with a Comparison to an $A_2$–Adenosine Receptor Regulating Coronary Blood Flow," *Biochem. Pharmacol.* 35(15):2467–2481 (1986).

Davies et al., "Pyrazolo [3,4–d]pyrimidines as Adenosine Antagonists," *Life Sci.* 34:2117–2128 (1984).

Elliot et al., "Structural analogs in the study of cytokinin action," *Chem. Abstracts* 79:98 Abstract No. 88241u (1973).

Fox and Kurpis, "Binding Characteristics of an Adenosine Receptor in Human Placenta," *J. Biol. Chem.* 258(11):6952–6955 (1983).

Fox et al., "Effect of substituents at the 9–position on cytokinin activity," *Chem. Abstracts* 79(19):78 Abstract No. 112299s (1973).

Fujii et al., "Hydrolytic Deamination versus Dimroth Rearrangement in the 9–Substituted Adenine Ring: Effect of an ω–Hydroxyalkyl Group at the 1–Position," *Chem. Pharm. Bull.* 34(3):1094–1107 (1986).

Geiger and Glavin, "Adenosine Receptor Activation in Brain Reduces Stress–Induced Ulcer Formation," *Eur. J. Pharmacol.* 115:185–190 (1985).

Glennon et al., "Mesoionic Xanthine Analogues: Antagonists of Adenosine Receptors," *J. Med. Chem.* 27:1364–1367 (1984).

Goldner and Carstens, "Synthesis of 9–substituted purine derivatives. I. 2,9–, 2,6,9– and 6,9–substituted purines," *Chem. Abstracts* 56(1):470 Abstract No. 470c–471e (1962).

Griffith et al., "8–phenyltheophylline: a potent $P_1$ purinoreceptor antagonist," *Eur. J. Pharmacol.* 75:61–64 (1981).

Hashizume et al., "Synthesis and biological activity of some new 6–benzylamino–9–alkylpurines," *Chem. Abstracts* 87(25):202 Abstract No. 195316j (1977).

Hill et al., "Attenuation of Adenosine $A_1$ Receptor Mediated Effects by N–0861, ($N^6$–Endonorboran–2–yl–9–Methyladenine) In Humans," *Drug Devel. Res.* 31(4):278 Abstract No. 1185 Presented at the 5th Intl. Symp. on Adenosine and Adenosine Nucleotides, Philadelphia, PA, (May 9–13, 1994).

Itaya et al., "Rate Study and Mechanism of the Dimroth Rearrangement of 1–alkoxy–9–alkyladenines and 1–alkyl–9–methyladenines," *Tetrahedron* 28:535–547 (1972).

Itaya et al., "Syntheses of N,N,3– and N,N,9–trialkyladenines by alkylation of N,N–dialkyladenines," *Chem. Abstracts* 93(15):716 Abstract No. 150216j (1980).

Jacobson et al., "[$^3$H]Xanthine amine congener of 1,3–dipropyl–8–phenylxanthine: An antagonist radioligand for adenosine receptors," *Proc. Natl. Acad. Sci. USA* 83:4089–4093 (1986).

Kamiya et al., "4–Deoxy–4–[(9H–purin–6–yl)amino]–D–erythronic acids," *Chem. Abstracts* 78:511 Abstract No. 97972q (1973).

Kamiya et al., "4–(9H–Purin–6–yl)amino–4–deoxy–D–erthyronate esters," *Chem. Abstracts* 78(13):472 Abstract No. 84764y (1973).

Kampe et al., "Adenosine Derivatives," *Republic of South Africa Patent Journal* 1(6):202–203 (1968).

Kelley et al., "6–(Alkylamino)–9–benzyl–9H–purines. A new class of anticonvulsant agents," *J. Med. Chem.* 31(3):606–612 (1988).

Kelley et al., "9–Benzyl–6–(dimethylamino)–9H–purines with antirhinovirus activity," *J. Med. Chem.* 31(10):2001–2004 (1988).

Kelley et al., "9–Benzyl–6–(dimethylamino)–9H–purines with antirhinovirus activity," *Chem. Abstracts* 109:730 Abstract No. 149466h (1988).

Kohjin Co., Ltd., "$N^6$,9–Disubstituted adenines," *Chem. Abstracts* 99(7):533 Abstract No. 53483k (1983).

Kos et al., "Anion Formation and Ring Opening of 9–Substituted Purines in Liquid Ammonia Containing Potassium Amide," *J. Org. Chem.* 48:850–855 (1983).

Kulaeva et al., "The effect produced by variations in the structure of cytokinins on their physiological activity," *Chem. Abstracts* 68(23):10032 Abstracts No. 104032g (1968).

Kusachi et al., "Dog Coronary Artery Adenosine Receptor: Structure of the $N^6$–Alkyl Subregion," *J. Med. Chem.* 28(11):1636–1643 (1985).

Londos et al., "Subclasses of external adenosine receptors," *Proc. Natl. Acad. Sci. USA* 77(5):2551–2554 (1980).

Martin et al., "(+)-$N^6$-Endonorbornan-2-yl-9-Methyladenine (N–0861) and its Enantiomers: Selective Antagonists of $A_1$–Adenosine Receptors in Guinea Pig Isolated Atria," *J. Pharmacol. Exp. Ther.* 265(1):201–206 (1992).

Martinson et al., "Potent Adensosine Receptor Antagonists that are Selective for the $A_1$ Receptor Subtype," *Molec. Pharmacol.* 31:247–252 (1986).

Montgomery and Temple, "Synthesis of Potential Anticancer Agents. IX. 9–Ethyl–6–substituted–purines," *J. Amer. Chem. Soc.* 79(19):5238–5242 (1957).

Myers and Zeleznick, "Alkylation of the Purine Nucleus by Means of Quaternary Ammonium Compounds. I. Tetraalkylammonium Hydroxides," *J. Org. Chem.* 28(8):2087–2089 (1963).

Nielsen and Pedersen, "Synthesis and Methylation of 6–Phenylaminopurines," *Chem. Scr.* 24:224–229 (1985).

Nielsen et al., "Phosphorus pentoxide in organic synthesis. XV. A new synthesis of adenines from 4–acylamino–1H–imidazole–5–carbonitriles," *Chem. Abstracts* 103:(2):Abstract No. 22351n (1985).

Olsson et al., "Coronary Vasoactivity of Adenosine in the Conscious Dog," *Circulation Res.* 45(4):468–478 (1979).

Peet et al., "Benzo[1,2-c:5,4-c']dipyrazoles: Non–Xanthine Adenosine Antagonists," *J. Med. Chem.* 31(10):2034–2039 (1988).

Petrova et al., "Synthesis of potentially antiblastic substances related to 5–hydroxytryptamine (serotonin). Products of the condensation of serotonin with some purine derivatives," *Chem. Abstracts* 70(1):382 Abstract No. 4056r (1969).

Pietraface and Blaydes, "Far–red light and coumarin induced changes in 9–methyl–$N^6$–benzyladenine metabolism by *Lactuca sativa* achenes," *Chem. Abstracts* 98:306 Abstract No. 86342w (1983).

Prasad et al., "Modification of the 5' Position of Pure Purine Nucleosides. 2. Synthesis and Some Cardiovascular Properties of Adenosine–5'–(N–substituted)carboxamides," *J. Med. Chem.* 23(3):313–319 (1980).

Psychoyos et al., "Inhibition by etazolate (SQ 20009) and cartazolate (SQ 65396) of adenosine–stimulated [$^3$H]cAMP formation in [2–$^3$H]adenine–prelabeled vesicles prepared from guinea pig cerebral cortex," *Biochem. Pharmacol.* 31(7):1441–1442 (1982).

Robins and Lin, "Potential Purine Antagonists IV. Synthesis of Some 9–Methyl–6–substituted purines," *J. Amer. Chem. Soc.* 79(2):490–494 (1957).

Shimada et al., "8–(Dicyclopropylmethyl)–1,3–dipropylxanthine: A Potent and Selective Adenosine $A_1$ Antagonist with Renal Protective and Diuretic Activities," *J. Med. Chem.* 34(1):466–469 (1991).

Skipper et al., "Structure–Activity Relationships and Cross–Resistance Observed on Evaluation of a Series of Purine Analogs Against Experimental Neoplasms," *Cancer Res.* 91:425–437 (1959).

Stein and Somani, "Cardiovascular Effects of Nucleoside Analogs," *Annals NY Acad. Sci.* 255:380–389 (1975).

Stein, H. H., "Ethyl Adenosine–5'–carboxylate. A Potent Vasoactive Agent in the Dog," *J. Med. Chem.* 16(11):1306–1308 (1973).

Trivedi et al., "$N^6$–Bicycloalkyladenosines with unusually high potency and selectivity for the $A_1$ adenosine receptor," *J. Med. Chem.* 32:8–11 (1989).

Ukena et al., "Analogs of Caffeine: Antagonist with Selectivity for $A_2$ Adenosine Receptors," *Life Sci.* 39(8):743–750 (1986).

Ukena et al., "Definition of subclasses of adenosine receptors associated with adenylate cyclase: interaction of adenosine analogs with inhibitory $A_1$ receptors and stimulatory $A_2$ receptors," *Can. J. Physiol. Pharmacol.* 65:365–376 (1987).

Ukena et al., "Effects of several 5'–carboxamide derivatives of adenosine on adenosine receptors of human platelets and rat fat cells," *Naunyn–Schmiedeberg's Arch. Pharmacol.* 327:36–42 (1984).

Ukena et al., "Functional Congeners of 1,3–Dipropyl–8–phenylxanthine: Potent Antagonists for Adenosine Receptors that Modulate Membrane Adenylate Cyclase in Pheochromocytoma Cells, Platelets and Fat Cells," *Life Sci.* 38(9):797–807 (1986).

Ukena et al., "$N^6$–substituted 9–methyladenines: A New Class of Adenosine Receptor Antagonists" *FEBS Lett.* 215(2):203–208 (1987).

Ukena et al., "Species differences in structure–activity relationships of adenosine agonists and xanthine antagonists at brain A1 adenosine receptors," *FEBS Lett.* 209(1):122–128 (1986).

Viskin et al., "Aminophylline for Bradyasystolic Cardiac Arrest Refractory to Atropine and Epinephrine," *Annals Int. Med.* 118:279–281 (1993).

Wesley, Jr., et al., "Effect of selective $A_1$ adenosine receptor antagonism of postdefibrillation cardiovascular depression: evidence for an antiadrenergic role of endogenous adenosine," *Cardiovascular Res.* 27:129–133 (1993).

Williams, M., "Purine Receptors in Mammalian Tissues: Pharmacology and Functional Significance," *Ann. Rev. Pharmacol. Toxicol.* 27:315–345 (1987).

Williams et al., "Interaction of putative anxiolytic agents with central adenosine receptors," *Can. J. Physiol. Pharmacol.* 59:897–900 (1981).

N6-SUBSTITUTED 9-METHYLADENINES: A NEW CLASS OF ADENOSINE RECEPTOR ANTAGONISTS

This application is a continuation of application Ser. No. 08/073,916, filed Jun. 8, 1993, now abandoned, which is a continuation of application Ser. No. 07/320,708, filed Mar. 8, 1989, now abandoned, which is a continuation-in-part of application Ser. No. 07/304,346, filed Jan. 31, 1981, now abandoned, which is a continuation-in-part of application Ser No. 07/042,383, filed Apr. 24, 1987, now abandoned, the contents of each of which are fully incorporated by reference.

SUMMARY OF THE INVENTION

Novel compounds and a method of using them to antagonize adenosine receptors are provided wherein the compounds are selected from the group of racemic mixtures or optically active compounds represented by the formula:

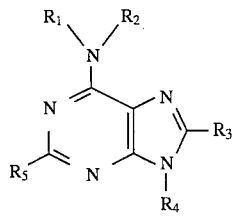

wherein $R_2$ is selected from the group consisting of cycloalkyl radicals having from 3 to 8, preferably 3 to 7, ring carbon atoms, alkyl radicals having from 1 to 10 carbon atoms, aryl radicals having from 6 to 13, preferably 6 to 10, carbon atoms, aralkyl radicals having from 7 to 14, preferably 7 to 10, carbon atoms,: and heteroatom- and halogen-substituted derivatives thereof wherein said heteroatom may be selected from the group consisting of nitrogen, phosphorus, sulfur and oxygen; $R_1$ may be hydrogen or $R_2$, and $R_3$ is selected from the group consisting of hydrogen, halogen, amine, carboxy, thio, sufonate, sulfonamide, sulfone, sulfoxamide, phenyl, alkyl-substituted amine, cycloalkyl-substituted amine, alkyl radicals having from 1 to 10 carbon atoms, and cycloalkyl radicals having from 3 to 8, preferably 5 to 6, ring carbon atoms. $R_4$ is selected from the group consisting of benzyl, phenyl, and alkyl groups comprising from 1 to 4 carbon atoms, wherein said alkyl group can be substituted with oxygen, for example ethers and alcohols. $R_5$ is selected from the group consisting of hydrogen; hydroxy; sulfonate; halogen; alkoxy and cycloalkoxy groups comprising 1 to 6 carbon atoms, wherein said alkoxy and cycloalkoxy groups can be substituted with phenyl; and amine, wherein said amine can be substituted with alkyl, cycloalkyl, or phenyl.

BACKGROUND OF THE INVENTION

Adenosine receptors have been divided into two subtypes, based on adenylate cyclase activity: $A_1$ ($R_i$) receptors mediate inhibition and $A_2$ ($R_a$) receptors mediate stimulation of adenylate cyclase activity. Some $N^6$-substituted adenosine analogs, like $N^6$-R-phenyl isopropyl adenosine (R-PIA) have very high affinity for $A_1$ adenosine receptors, but at $A_2$ receptors 5'-N-ethylcarboxamido-adenosine (NECA) is more potent than $N^6$-substituted analogs. Alkylxanthines, such as caffeine and theophylline, are the best known antagonists at adenosine receptors.

Adenine was generally believed to have no effect on adenosine receptor-controlled systems. However, it was found that at low concentrations adenine displays specific competitive antagonism of adenosine-induced cyclic Amp accumulation in a human fibroblast cell line. Methylation of adenine at the 9-position increases potency about 4-fold in this assay. At higher concentration, both compounds show nonspecific inhibitory activity.

DETAILED DESCRIPTION OF THE INVENTION

The compounds of this invention are selected from the group of compounds, including the racemic mixtures or optically active compounds represented by the general formula:

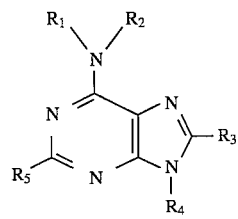

wherein $R_2$ is selected from the group consisting of cycloalkyl radicals having from 3 to 8, preferably 3 to 7, ring carbon atoms, alkyl radicals having from 1 to 10 carbon atoms, aryl radicals having from 6 to 13, preferably 6 to 10, carbon atoms, aralkyl radicals having from 7 to 14, preferably 7 to 10, carbon atoms, and heteroatom- and halogen-substituted derivatives thereof wherein said heteroatom may be selected from the group consisting of nitrogen, phosphorus, sulfur and oxygen; $R_1$ may be hydrogen or $R_2$, and $R_3$ is selected from the group consisting of hydrogen, halogen, amine, carboxy, alkyl radicals having 1 to 10 carbon atoms, cycloalkyl radicals having from 3 to 8, preferably 5 to 6, ring carbon atoms, thio, sulfonate, sulfonamide, sulfone, sulfoxamide, phenyl, alkyl-substituted amine, and cycloalkyl substituted amine. $R_4$ is selected from the group consisting of benzyl, phenyl, and alkyl groups comprising from 1 to 4 carbon atoms, wherein said alkyl group can be substituted with oxygen, for instance ethers and alcohols. $R_5$ is selected from the group consisting of hydrogen; hydroxy; sulfonate; halogen; alkoxy and cycloalkoxy groups comprising 1 to 6 carbon atoms, wherein said alkoxy and cycloalkoxy groups can be substituted with phenyl; and amine, wherein said amine can be substituted with phenyl and alkyl and cycloalkyl groups comprising 1 to 6 carbon atoms.

Preferred compounds are those wherein $R_1$ is hydrogen; wherein $R_2$ is endo-2-Norbornyl or cyclopentyl; wherein $R_3$ is bromine, chlorine, amino, hydrogen, thio, cyclopentyl or cyclopentylamine; wherein $R_4$ is methyl, ethyl, 2-hydroxyethyl, phenyl, or 2-hydroxyethoxy methyl; and wherein $R_5$ is hydrogen, hydroxy, chlorine or fluorine.

The following is a list of compounds, including the racemic mixtures or optically active species of which are useful in the practice of the present invention. This list is intended to be illustrative and the scope of the invention is not limited to compounds named therein:

$N^6$-Cyclobutyl-9-Methyl Adenine (MA)
$N^6$-Cyclopentyl-9-MA
$N^6$-Methylcyclopentyl-9-MA
$N^6$-Cyclohexyl-9-MA
$N^6$-Methyl-9-MA
$N^6$-3-pentyl-9-MA $N^6$-Phenyl-9-MA
$N^6$-2-Fluorophenyl -9-MA
$N^6$-Benzyl-9-MA
$N^6$-2-Phenethyl-9-MA
$N^6$-2- (3,4,5-Trimethoxyphenyl) ethyl-9-MA
$N^6$-2-(3-Pyridylethyl)-9-MA
$N^6$-2-(3-Thienylethyl)-9-MA
$N^6$-R-1-Phenyl-2-propyl-9-MA
$N^6$-S-1-Phenyl-2-propyl-9-MA
$N^6$-(endo-2-Norbornyl)-9-MA
$N^6$-[endo-(1R,2S,4S)-2-Norbornyl]-9-MA
$N^6$-[endo-(1S,2R,4R)-2-Norbornyl]-9-MA
$N^6$-1-(2-Thienyl)-2-butyl-9-MA
$N^6$-(exo-2-Norbornyl)-9-MA
$N^6$-2,2-diphenylethyl-9-MA
$N^6$-2-phenylethyl-9-MA
$N^6$-2-(2-chlorophenyl)ethyl-9-MA
$N^6$-indanyl-9-MA
$N^6$-2-aminoethyl-9-MA
$N^6$-(N,N-Dimethylaminoethyl))-9-MA
$N^6$-R-1-phenyl-1-ethyl-9-MA
$N^6$-S-1-phenyl-1-ethyl-9-MA
$N^6$-2-thienyl-9-MA
$N^6$-(4-chloro-2-methyl phenyl)-9-MA
$N^6$-2-(3-ethylindole)-9-MA
$N^6$-(1-methyl-2-phenylethyl)-9-MA
$N^6$-(1-methyl-2-phenoxyethyl)-9-MA
$N^6$-1-carboxy-1-butyl-9-MA
$N^6$-(endo-2-norbornyl)-2-chloro-9-MA
$N^6$-(endo-2-norbornyl)-8-cyclopentyl-9-MA
$N^6$-(endo-2-norbornyl)-8-hydroxy-9-MA
$N^6$-(endo-2-norbornyl)-8-bromo-9-MA
$N^6$-[endo-(1R,2S,4S)-2-Norbornyl]-8-bromo-9-MA
$N^6$-[endo-(1S,2R,4R)-2-Norbornyl]-8-bromo-9-MA
$N^6$-(endo-2-norbornyl)-8-amino-9-MA
$N^6$-(endo-2-norbornyl)-8-carboxy-9-MA
$N^6$-cyclopentyl-8-cyclopentyl-9-MA
$N^6$-(endo-2-norbornyl)-9-[(2-hydroxyethoxy)methyl]adenine
$N^6$-(endo-2-norbornyl)-8-thio-9-MA
$N^6$-(endo-2-norbornyl)-8-chloro-9-MA
$N^6$-[endo-(1R,2S,4S)-2-Norbornyl]-8-chloro-9-MA
$N^6$-[endo-(1S,2R,4R)-2-Norbornyl]-8-chloro-9-MA
$N^6$-(endo-2-norbornyl)-8-sulfonate-9-MA sodium salt
$N^6$-(endo-2-norbornyl)-2-hydroxy-9-MA
$N^6$-(endo-2-norbornyl)-8-cyclopentylamine-9-MA
$N^6$-(endo-2-norbornyl)-8-propylamine-9-MA
$N^6$-(endo-2-norbornyl)-9-phenyl adenine
$N^6$-cyclopentyl-2-chloro-9-MA
$N^6$-phenyl-2-chloro-9-MA
$N^6$-cyclopentyl-9-phenyl adenine
$N^6$-R-1-phenyl-2-propyl-9-phenyl adenine
$N^6$-S-1-phenyl-2-propyl-9-phenyl adenine
$N^6$-[(3-chloro-endo-2-norbornyl)]-9-MA
$N^6$-phenyl-9-phenyl adenine
2-ethoxy-9-MA
2-propoxy-9-MA
2-butoxy-9-MA
2-isopropoxy-9-MA
2-(2-butoxy)-9-MA
2-(2-methyl propoxy) 9-MA
2-pentoxy-9-MA
2-(2-phenylethoxy) 9-MA
2-phenylamino-9-MA
9-hydroxyethyladenine
$N^6$-cyclopentyl-9-benzyl adenine
$N^6$-cyclohexyl-9-ethyl adenine It is essential that the compound selected for use in the method of the present invention be an optically active compound or racemic mixture thereof capable of inhibiting activity of adenosine receptors, e.g., in a human. In particular it is found that the isomers of $N^6$-(endo-2-Norbornyl)-9 methyladenines are especially preferred for inhibiting activity of $A_1$ adenosine receptors. One group of these preferred stereoisomers has the general formula

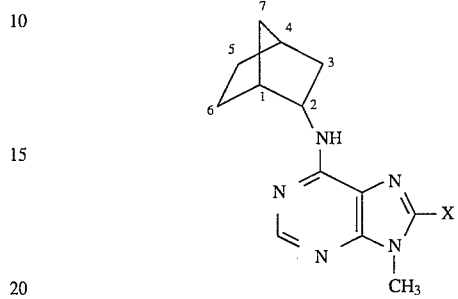

wherein X is halogen or hydrogen. This group of preferred stereoisomers is designated as the $N^6$-[endo(1R,2S,4S)-2-Norbornyl]-9 methyladenines. For example, $N^6$-[endo(1R,2S,4S)-2-Norbornyl]-8-bromo-9-MA and $N^6$-[endo(1R,2S,4S)-2-Norbornyl]-8-chloro-9-MA. The enantiomers of these compounds are the stereoisomers, having the general formula

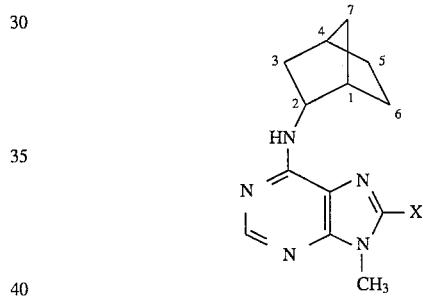

wherein X is hydrogen or halogen. The latter group of preferred stereoisomers is designated as the N6[endo-(1S,2R,4R)- 2-Norbornyl]-9-methyladenines, for example $N^6$[endo-(1S,2R,4R)-2-Norbornyl]-8-bromo-9-methyladenine and $N^6$[endo-(1S,2R,4R)-2-Norbornyl]-8-chloro-9-methyladenine.

The preparation of 9-methyl adenines is well known. See R. K. Robins, K. J. Dille and B. E. Christensen, J. Org. Chem., 19, 930 (1954); R. K. Robins and H. H. Lin, J. Am. Chem. Soc., 79, 490 (1957; and J. A. Montgomery and Carroll Temple, Jr., J. Am. Chem. Soc., 79, 5238 (1957).

Preparation of $N^6$-Cyclopentyl-9-Methyl Adenine

To prepare $N^6$-cyclopenyl-9-methyl Adenine the following additional steps were taken. A mixture of 6-chloro-9-methyl Adenine (0.82 g) , cyclopentylamine (0.52 ml) , trimethylamine (0.53 ml) and ethanol. (60 ml), was refluxed for 24 hours. The solution was concentrated in vacuo to a yellow syrup. The syrup was passed through a C-18 column to give 0.78 g or 74% yield of with m.p. 108°–109° C. $^1$HNMR(Me$_2$SO-d$_6$): δ1–2 (m, 9 H); 3.7 (S, CH$_3$); 7.6(d, NH); 8.1(S,1H); 8.2(S,1H).

Preparation of $N^6$-3-Pentyl-9-Methyladenine

A mixture of 6-chloro-9-methyladenine (1.5 g), 3-pentylamine (1.3 ml), trimethylamine (1.3ml) and ethanol (60 ml),

Preparation of N$^6$-(endo-2-Norbornyl)-9-Methyladenine

A mixture of 1.5 g 6-chloro-9-methyl Adenine, 1.75 g endo-2-aminonobornane, 2.9 ml trimethylamine and 60 ml ethanol was refluxed overnight. The solution was then concentrated in vacuo and the remainder was passed through C-18 prepchromatography to give 1.6 g (75% yield) m.p. 130°–131° C. $^1$HNMR(Me$_2$SO-d$_6$): δ1–2.6(n,10 H); 3.8(S, CH$_3$); 4.1(m,1H); 7.2(S,NH); 7.4(S,1H); 7.6(S,1H).

Preparation of N$^6$-(endo-2-Norbornyl)-8-Bromo-9MA

To a stirred suspension of N$^6$-(endo-2-norbornyl)-9-MA (6 g, 24.66 mmoles) 2,n 150 mL of 1M sodium acetate buffer (pH 3.9) was added a solution of bromine (3.0 ml) in 300 ml of 1M sodium acetate buffer (pH 3.9). The mixture was stirred overnight and the resulting precipitate was filtered and washed with water. To the residue was added silica gel and the suspension was evaporated to a powder. The powder was added to a silica gel column (150 g, packed with petroleum ether). The purine was eluted with 10% to 25% ethylacetate in petroleum ether. Evaporation of the appropriate fractions gave 6.7 g, 84% yield of N$^6$-(endo-2-Norbornyl)-8-Bromo-9-MA Preparation of N$^6$-(endo-2-Norbornyl)-8-Azido-9-MA To a solution of N$^6$-(endo-2-Norbornyl)-9-Bromo-9-MA (0.72 g, 2.23 mmoles) in DMF was added sodium azide (0.91 g, 13.98 mmoles). The mixture was heated at 70°–80° C. overnight. The crude was dissolved in water, extracted with ethyl acetate, and then dried over magnesium sulfate and the organic phase was evaporated in vacuo to give 0.62 g, 98% yield.

Preparation of N$^6$-(endo-2-Norbornyl)-8-Amino-9-MA

The crude product, N$^6$-(endo-2-Norbornyl)-8-Azido-9-MA (0.5 g, 1.75 mmole) was dissolved in ethanol. The solution, in presence of 10% palladium on charcoal (1 g), was shaken with H$_2$ at 35 atm overnight. The suspension was filtered and evaporated to a small volume, and then poured through a C-18 column (HPLC) to give 0.36 g 80% yield of N$^6$-(endo-2-norbornyl)-8-Amino-9-MA.

Preparation of N$^6$-(endo-2-Norbornyl)-8-Oxo-9-MA

To a mixture of N$^6$(endo-2-Norbornyl)-9-Bromo-9-MA (0.15 g, 0.62 mmole) in 12 ml acetic acid was added sodium acetate (0.5 g) and 1.2 ml acetic anhydride. The mixture was allowed to reflux overnight. The mixture was then evaporated under vacuo and purified on a chromatotron using CHCl$_3$, stepping to 2% ethanol, and finally to 4% ethanol on 2 mm plate giving 90 mg, 75% yield of N$^6$-(endo-2-Norbornyl)-8-Oxo-9-MA.

Preparation of N$^6$-(endo-2-Norbornyl)-8-Cyclopentylamine-9-MA

To a solution of N$^6$-(endo-2-Norbornyl)-8-Bromo-9-MA (0.5 g, 1.55 mmols) in 20 ml ethanol was added 20ml of cyclopentylamine; the reaction mixture was refluxed overnight. The mixture was then evaporated under vacuo and passed through a C-18 column (HPLC) to give 0.32 g, 77% yield of N$^6$-(endo-2-Norbornyl)-8-Cyclopentylamine-9-MA.

Preparation of N$^6$-(endo-2-Norbornyl)8-Bromo-2-Chloro-9-MA

N$^6$(endo-2-Norbornyl)2-Chloropurine was first prepared as follows: A mixture of 2,6-dichloropurine (5.0 g, 26.45 mmoles) endo-2-aminobornane hydrochloride (5.0 g, 33.86 mmoles) and trimethylamine (10 ml) in absolute ethanol was refluxed for 48 hours. The solution was then cooled to room temperature and evaporated in vacuo to a white solid. The white solid was washed with water and dried to yield 6.0 g, 84% yield of N$^6$-(endo-2-Norbornyl)2-Chloropurine used as is with no further purification for next step.

A mixture of N$^6$-(endo-2-Norbornyl)-2-chloropurine (5.0 g, 18.96 mmoles), triethyl ammonium hydroxide (18.9 ml), and methyl iodide (1.41 ml, 22.68 mmoles) in dichloromethane was heated to 35° C. for 24 hours. The solution was then evaporated in vacuo and the syrup was crystallized in methanol to give 4.0 g, 76% yield of N$^6$-(endo-2-Norbornyl)2-chloro-9-MA.

To a stirred solution of N$^6$-(endo-2-Norbornyl)-2-chloro-9-MA (4.3 g, 14.4 mmoles) in acetate buffer (1 molar acetic acid and 1 M sodiums acetate mixture, 45:1 ratio respectively; pH=3.9) was added dropwise Bromine (3.12 g, 19.56 mmoles) dissolved in the acetate buffer. The reaction mixture was stirred for 72 hours; the mixture was then filtered and the solid material collected was eluted from ethyl acetate/petroleum ether on silica gel column to yield 4.9 g, 85% of N$^6$-(endo-2-Norbornyl)8-Bromo-2-Chloro-9-MA.

Preparation of N$^6$-(endo-2-Norbornyl)-8-Cyclopentyl-9-MA

To a vigorously stirred solution of 2 g (12.2 mmoles) of 4-methylamino-5-amino-6-chloropyrimidine in CHCl$_3$ was added dropwise over a period of 20 minutes cyclopentane carbonyl chloride (1.6 g, 12.2 mmoles). The mixture was stirred overnight and then evaporated in vacuo to a yellow syrup. The syrup was then dissolved in methanol and purified through a C-18 column (HPLC) to give 2.2 g, 71% yield of 4 methylamino-6-chloro-5-cyclopentylamido-pyrimidine.

4-methylamino-6-chloro-5-cyclopentylamido-pyrimidine 2.2 g, 8.6 mmoles) was refluxed in POCl$_3$ for approximately 2 hours. The solution was concentrated in vacuo to a syrup. The syrup was added dropwise twice. The aqueous mixture was then extracted with chloroform. The organic layer was evaporated and the syrup was passed through a C-18 column (HPLC) giving 1.25 g, 63% yield of 8-cyclopentyl-6-chloro-9-methyladenine.

A mixture of 8-cyclopentyl-6-chloro-9-methyladenine (0.48 g 2.0 mmoles) and endo-2-aminonorbornane hydrochloride (0.5 g, 3.4 mmoles) in absolute ethanol was refluxed for 48 hours. The mixture was then evaporated in vacuo and purified through a C-18 column (HPLC) to give 0.45 g, 71% yield of N$^6$ (endo-2-Norbornyl)-8-cyclopentyl-9-MA.

Preparation of N⁶-(endo-2-Norbornyl)-8-Chloro-9-MA

A mixture of N⁶-(endo-2-Norbornyl)-8-bromo-9-MA (1.25 g, 3.7 mmoles) and POCl3 was refluxed for 1 hour. Then the phosphorous oxychloride was removed in vacuo and the yellow solid was passed through a C-18 column (HPLC) to give 0.96 g, 84% yield of N⁶-(endo-2-Norbornyl)-8-chloro-9-MA.

Preparation of N⁶-(endo-2-Norbornyl)-9-[(2-hydroxyethoxy)methyl]purine.

To a solution of 6-chloropurine (6 g, 38.8 mmoles) in DMF was added sodium hydride 60% (0.93 g) over 1.5 hour period. (2-acetoxyethoxy)methyl bromide was then added at room temperature; the reaction mixture was allowed to stir for 2 hours under $N_2$ atmosphere. $H_2O$ was added and the product was extracted with ethyl acetate. The organic phase was dried over $MgSO_4$, filtered, and evaporated in vacuo to give a light yellow solid 7.1 g, 68% yield of 9-[(2-Acetoxyethoxy)methyl]-6-chloro-purine. The crude was used without further purification.

To a solution of 9-[(2-acetoxyethoxy)methyl]-6-chloropurine (5.1 g, 18.8 mmoles) in ethanol and trimethylamine was added endo-2-aminonorbornane hydrochloride (4.0 g, 27.1 mmoles). The mixture was refluxed in vacuo and the residue was purified by HPLC to give 4.70 g, 77% yield of N⁶-(endo-2-Norbornyl)-9-[( 2-acetoxyethoxy)methyl]purine.

A solution of N⁶-(endo-2-Norbornyl)-9-[(2-acetoxyethoxy) methyl]purine (3.75 g, 10.8 mmoles) in methanol was saturated with $NH_3$ gas under $N_2$. The mixture was stirred overnight, then evaporated in vacuo to give 2.03 g, 62% yield of N⁶-(endo-2-Norbornyl)-9-[(2-hydroxyethoxy)methyl]purine.

Preparation of 1R, 2S, 4S- endo-2-Aminonorbornane

A) As is well known in the art[1], resolution of chiral amines may be accomplished by preparing diastereomeric salts with chiral acids. The resultant diastereomeric salts show different physical properties, enabling separation by methods such as fractional crystallization or chromatography. Thus, a mixture of endo-2-aminonorbornane isomers are reacted with chiral acids (e. g., Tartaric Acid, Mandelic Acid) to form diastereomeric salts and subjected to fractional crystallization. Alternatively, chromatographic separation of these salts (e.g., silica gel) may be employed.

B) Chromatography employing chiral stationary phases (e.g., Pirkle, Beta-cyclodextrin columns) may be used to isolate the above isomers.

C) The individual isomers may be prepared individually starting from (+) and (−) endo-2-carboxylnorbornane-2,3. These carboxylic acids may be individually converted to the above isomers by the Curtius rearrangement[4,5], wherein the carboxylic acid is replaced by an amino group. See also Berson, J., et al., J. Amer. Chem. Soc., 81, 4094-8 (1959) and J. Amer. Chem. Soc., 83, 3986–3997 (1961).

Preparation of 1R,2S,4S- and 1S,2R,4R-(N⁶-endo-2-Norbornyl-9-methyladenine

The above prepared amines are reacted with 6-chloro-9-methyladenine as previously described.

REFERENCES

1. March, J., Advanced Organic Chemistry: Reactions, Mechanisms and Structure, Third Ed., John Wiley and Sons, 104, 1985.
2. Scheidegger, U. et al, J. Amer. Chem. Soc, 89, 894 (1967).
3. Evans, D. A., et al., J. Amer. Chem. Soc., 110, 1238 (1988).
4. Beilstein 12 (3), 160.
5. March, 984, 1985.

For purposes of this invention, designation of an optically active stereoisomer shall mean that one enantiomer is present in excess of the other enantiomer. Preferably, the mixture is greater than 90 mole percent of one enantiomer, most preferably one enantiomer is substantially pure, i.e, greater than 99 mole percent.

The invention is further illustrated by the following examples which are illustrative of various aspects of the invention. These examples are not intended as limiting the scope of the invention as defined by the appended claims.

PHARMACOLOGIC TESTING

A series of N⁶-substituted 9-methyladenines were assayed as adenosine antagonists in $A_1$ and $A_2$ test systems (Ukena, et al, FEBS Lett. 215(2), 203–208, 1987). For activity at $A_1$ receptors, compounds were tested as inhibitors of the binding of N⁶-E-[3H]-Phenylisopropyladenosine in rat brain membranes and for their ability to prevent R-PIA-induced inhibition of adenylate cyclase in rat fat cell membranes. For activity at $A_2$ receptors, compounds were tested as antagonists of NECA-stimulated adenylate cyclase in membranes of human platelets and rat PC12 cells.

It is known that $A_1$ receptors influence inhibition of adenylate cyclase in fat, brain and heart cells; whereas $A_2$ receptors stimulate adenylate cyclase in endothelial and smooth muscle cells. (See John W. Daly, et al, "Structure-Activity Relationship for N⁶-Substituted Adenosines at a Brain $A_1$-Adenosine Receptor With A Comparison to an $A_2$-Adenosine Receptor Regulating Coronary Blood Flow," Biochemical Pharmacology, Vol. 35. No. 15, pp. 2467–2471 (1986)).

The results summarized below in Table I show that N⁶ substitution can markedly increase the potency of 9-methyladenine at adenosine receptors. The lower apparent affinity values ($K_B$, $K_i$) identify the most potent compounds. The most pronounced effect is seen at $A_1$ receptors. For example, N⁶-Cyclopentyl-9-methyladenine is at least 100-fold more potent than 9-methyladenine at $A_1$ receptors. At $A_2$ receptors, this compound is 5-fold more potent than 9-methyladenine in the human platelet assay. Thus, this data demonstrates the activity of a novel series of adenosine antagonists.

TABLE 1

|  | $A_2$ Effects $K_B$ (μM) vs NECA Stimulation (Adenylate Cyclase) | | $A_1$ Effects | |
|---|---|---|---|---|
|  | | | $K_B$ (μM) vs PIA INHIBITION (Adenylate Cyclase) | $K_i$ (μM) vs [$^3$H] PI (Binding) |
|  | (A) | (B) | (C) | (D) |
| 1. Adenine | 760 | 570 | >1000 | >100 |
| 2. 9-Methyladenine (9-MA) | 24 | 24 | 112 | 106 |
| $N^6$-substituted 9-methyladenines | | | | |
| 3. $N^6$-cyclobutyl-0-MA | 5.5 | 23 | 0.89 | 1.2 |
| 4. $N^5$-Cyclopentyl-9-MA | 4.9 | 25 | 1.3 | 0.54 |
| 5. $N^6$-Methylcylopentyl-9-MA | 45 | 56 | 9.0 | 2.5 |
| 6. $N^6$-Cyclohexyl-9-MA | 7.4 | 21 | 0.65 | 0.94 |
| 7. $N^6$-Methyl-9-MA | 150 | 130 | 220 | >100 |
| 8. $N^6$-3-Penytl-9-MA | 11 | 53 | 7.6 | 3.3 |
| 9. $N^6$Phenyl-9-MA | 21 | 107 | 10 | 25 |
| 10. $N^6$-2-Fluorophenyl-9-MA | 11 | 29 | 17 | 8.5 |
| 11. $N^6$-2-Benzyl-9-MA | 57 | 100 | 49 | 17 |
| 12. $N^6$-2-Phenethyl-9-MA | 170 | 120 | >300 | >100 |
| 13. $N^6$-2-(3,4,5-Trimethoxyphenylethyl)-9-MA | 23 | 40 | 122 | >100 |
| 14. $N^6$-2-(3-Pyridylethyl)-9-MA | 92 | 117 | 96 | 41 |
| 15. $N^6$-2-(3-Thienylethyl)-9-MA | 14 | 25 | 24 | 20 |
| 16. $N^6$R-1-Phenyl-2-propyl-9-MA | 13 | 25 | 7.2 | 2.5 |
| 17. $N^6$-S-1-Phenyl-2-propyl-9-MA | 23 | 74 | 23 | 10 |

(A) - Human Platelet Membranes
(B) - Rat PC12 Membranes
(C) - Rat Fat Cell Membranes
(D) - Rat Brain Membranes

FURTHER FUNCTIONAL ASSAYS

To test the selectivity of the compounds of the invention, in vitro assays were conducted utilizing model tissues that are thought to contain homogenous populations of either the $A_1$ or $A_2$ adenosine receptors. Four examples were characterized by their ability to antagonize competitively the action of adenosine agonists in eliciting two responses: the reduction in force of contraction of guinea pig atrium ($A_1$); and the decrease in the contractile tone of the guinea pig taenia caecum ($A_2$).

The left atria from male guinea pigs were isolated, suspended between two punctate electrodes, and placed in a 20 ml organ bath that contained Krebs-Hensileit solution that was continuously gassed with 95% $O_2$+5% $CO_2$ and maintained at 31° C. The resting tension was one gram. The atria were stimulated electrically at 1 Hz, 1 msec duration pulses at supramaximal voltage. The force of contraction was recorded isometrically.

Taenia from the guinea pig caecum were cut into lengths of 1.5–2 cm. The tissues were suspended in a 20 ml organ bath containing de Jalon's solution that was gassed with 95% $O_2$+5% $CO_2$ and maintained at 31° C. The resting tension was 1.5 g. The contractile response was measured isotonically. Tissues were contracted with $10^{-7}$M 5-methylfurmethide and allowed sufficient time to reach a stable contraction before addition of adenosine agonists.

The ability of the compounds to antagonize the effects of agonists was analyzed using modified Schild plots.

Although there was some sensitization of the tissue, i.e. addition of the agonist produced a larger response in the presence of high concentrations of the subject compounds, $N^6$-3-Pentyl-9-MA, $N^6$-Cyclopentyl-9-MA and $N^6$-(endo-2-Norbornyl)-9-MA did not competitively antagonize the effects of adenosine agonists in relaxing the taenia caecum. Sensitization is also observed when using high concentrations of 8-phenyltheophylline (8-PT), a non-selective adenosine receptor antagonist. 8-PT did antagonize the effects of agonists at low concentrations. The lack of competitive antagonism by the other I compounds suggests that the latter compounds do not interact appreciably with $A_2$-adenosine receptors and are, thus, selective for $A_1$ adenosine receptors.

However, $N^6$-3-Pentyl-9-MA, $N^6$-Cyclopentyl-9-MA, $N^6$-(endo-2-Norbornyl)-9-MA and $N^6$-4-(2-thienyl)-3-butyl)-9-MA all were found to be competitive antagonists at adenosine receptors in the atria. $N^6$-3-Pentyl-9-MA and $N^6$-1-(2-thienyl)-2-butyl-9-MA also produced increases in basal force of contraction in the atria. Affinity constants (pKB) for the present compounds determined using known methods are summarized in Table 2 below:

TABLE 2

| Drug | $pK_B$ |
|---|---|
| $N^6$-3-Pentyl-9-MA | 5.4 ± 0.14 |
| $N^6$-Cyclopentyl-9-MA | 6.17 ± 0.11 |
| $N^6$-(endo-2-Norbornyl)-9-MA | 6.28 ± 0.09 |
| $N^6$-1-(2-Thienyl)-2-butyl)-9-MA | 5.36 ± 0.1 |

These results show that the above examples display selectivity towards the $A_1$ adenosine receptor, with $N^6$-(endo-2-Norbornyl)-9-MA being the most potent antagonist.

IN VIVO ASSAY

In vitro selectivity of the present antagonists was confirmed by in vivo tests on rat heart rate and blood pressure, the former associated with $A_1$ receptors and the latter associated with $A_2$ receptors.

Rats were anesthetized with urethan and blood pressure was monitored via a carotid cannula. Drug injections were made intravenously through a jugular cannula. Blood pressure, EGC, and heart rate were recorded on a Grass polygraph.

Adenosine produced a dose dependent decrease in blood pressure and heart rate, with a concommitant increase in the P-R interval of the ECG. . Administration of $N^6$-(endo Norbornyl) -9-methyladenine attenuated the effects of subsequently administered adenosine on all parameters measured. At high doses, adenosine causes heart block; this effect was also substantially reduced by the agonist. Due to the short duration of action and direct route of administration of adenosine, it is often difficult to determine whether adenosine decreased blood pressure by causing peripheral vasodilation or by reducing cardiac output. To overcome these problems, NECA (5'-N-ethylcarboxamide adenosine), which is longer-acting and selective for $A_2$ adenosine receptors, was used as an adenosine receptor agonist. Prior administration of N-0861 attenuated the effects of NECA on the heart while minimally affecting the NECA-induced decrease in blood pressure. These results show that $N^6$-endo-2-Norbornyl)-9-methyladenine is a cardio-selective adenosine receptor antagonist in vivo and support the data above showing selectively of the N-6 substituted 9-methyladenines of the invention as $A_1$ adenosine receptor antagonists.

FURTHER RECEPTOR AFFINITY ASSAYS

Further tests to discover the affinities of test compounds at $A_2$ receptors were conducted. [3H]-N-ethylcarboxamido adenosine ([3H-]-NECA) was used as the radio-ligand, bovine caudate was the source of membranes, and the assay buffer was 50 mM Tris; 10 mMMgCl$_2$, pH 7.4.

To provide bovine caudate nuclei, bovine brains were obtained fresh from a local slaughterhouse. The caudate nuclei were dissected out and homogenized in Buffer A (50 mm Tris; 1 mm Na2-EDTA; 5 mm KCl; 1 mm MgCl$_2$; 2 mm CaCl$_2$; pH 7.4) using a Brinkman Polytron. The homogenate was centrifuged at 40,000×g for 20 minutes and washed once. The pellet was resuspended in Buffer A, incubated at 37° C. for 15 minutes, then centrifuged. The pellet was washed once more, resuspended to a protein concentration of 5–10 mg/ml in Buffer A and frozen at −70° C. until use.

The $A_2$ assays also contained 50 nM cyclopentyl-adenosine to block the binding of [3H]-NECA to $A_1$ receptors (Bruns et al, 1986) and 1 unit/ml adenosine deaminase to degrade endognous adenosines. Varying concentrations of test compounds were incubated with the appropriate radio-ligand and membrane source for 1 hr at room temperature.

Assays were terminated by filtration over Whatman GF/B filters that had been pre-soaked with 0.1% polyethyleneimine using a 24 port Brandell cell havester. The filters were washed three times with 3 ml of ice cold buffer and transfered to plastic scintillation vials to which 4 ml of Beckman Ready protein scintillation cocktail was added. The tubes were shaken and counted in a Beckman 3801 scintillation counter that converted cpm to dpm.

Data were analyzed by utilizing the Ligand, commercial computer program (Munson and Rodbard, 1980).

The results of these tests, expressed as the molar concentration of test compound needed to displace 50 percent of the [3HI-CHA radioligand from rat cortical $A_1$ receptors, are summarized in Table 3 below:

TABLE 3

Adenosine Antagonists

| Sample No. | Name | Rat Cortical Binding Constant Ki (M) |
|---|---|---|
| 0861 | $N^6$-(endo-2-norbornyl)-9-MA | $11.6 \times 10^{-8}$ |
| 0913 | $N^6$-(endo-2-norbornyl)-2-chloro-9-MA | $10.5 \times 10^{-8}$ |
| 0966 | $N^6$-2,2-diphenylethyl-9-MA | $>10^{-5}$ |
| 0967 | $N^6$-2(2-chlorophenylethyl)9-MA | $>10^{-5}$ |
| 0982 | $N^6$-2-Aminoethyl-9-MA | $>10^{-5}$ |
| 0983 | $N^6$-(2,2-N-dimethylethyl)-9-MA | $>10^{-5}$ |
| 0840 | $N^6$-cyclopentyl-9-MA | $37.5 \times 10^{-8}$ |
| 0984 | $N^6$-R-1-phenyl-1-ethyl-9-MA | $>10^{-5}$ |
| 0985 | $N^6$-S-1-phenyl-1-ethyl-9-MA | $>10^{-4}$ |
| 0986 | $N^6$-S-1-phenyl-2-propyl-9-MA | $>10^{-5}$ |
| 0987 | N6 2-thienyl-9-MA | $>10^{-4}$ |
| 0988 | N6(4-chloro-2-methylphenyl)-9-MA | $>10^{-5}$ |
| 0989 | $N^6$-2-(3-ethylindole)-9-MA | $>10^{-5}$ |
| 0990 | $N^6$-2-(phenethyl)9-MA | $>10^{-5}$ |
| 1001 | $N^6$-(endo-2-norbornyl)-8-oxo-9-MA | $\approx 10^{-5}$ |
| 1002 | $N^6$-2-(3,4,5-trimethoxyphenyl)ethyl-9-MA | $>10^{-5}$ |
| 1003 | $N^6$-(endo-2-norbornyl)-8-bromo-9-MA | $1.3 \times 10^{-8}$ |
| 1004 | $N^6$-1-carboxy-1-butyl-9-MA | $>10^{-4}$ |
| 1005 | $N^6$-(endo-2-norbornyl)-8-amino-9-MA | $87 \times 10^{-8}$ |
| 1006 | $N^6$-(endo-2-norbornyl)-8-carboxy-9-MA Sodium Salt | $>10^{-5}$ |
| 1059 | $N^6$-(endo-2-norbornyl)9-[(2 hydroxyethoxy) methyl]adenine | $49 \times 10^{-8}$ |
| 1060 | $N^6$-(endo-2-norbornyl)-8-thio-9-MA | $37 \times 10^{-8}$ |
| 1061 | $N^6$-(endo-2-norbornyl)-8-chloro-9-MA | $1.5 \times 10^{-8}$ |
| 1062 | $N^6$-(endo-2-norbornyl)-8-sulfonate-9-MA Sodium Salt | $>10^{-4}$ |
| 1063 | $N^6$-(Endo-2-norbornyl)-2-oxo-9-MA | $112 \times 10^{-8}$ |
| 1064 | $N^6$-(endo-2-norbornyl)-8-cyclopentylamine-9-MA | $190 \times 10^{-8}$ |
| 0964 | $N^6$-(endo-2-norbornyl)-8-cyclopentyl-9-MA | $24 \times 10^{-8}$ |
| 0965 | $N^6$-cyclopentyl-8-cyclopentyl-9-MA | $14.1 \times 10^{-8}$ |
| 0978 | $N^6$-(exo-2-norbornyl)-9-MA | $43 \times 10^{-8}$ |

The compounds in Table 3 for which a solution having a concentration greater than $10^{-5}$M was required to displace 50 percent of the radioligand are deemed ineffective as $A_1$ adenosine receptor antagonists.

In further experiments designed to determine the selectivity of $N^6$-endo-2-Norbornyl-9-methyl adenine at $A_1$ receptors, [3HI -cyclohexyladenosine ( [3H]-CHA) was used as the radioligand, rat cortical membranes were the receptor source, and the assay buffer was 50 mM Tris; 2 mM MgCl$_2$ pH 7.4.

Male Sprague Dawley rats were killed by decapitation and the brains removed. The cerebral cortices were homogenized in 50 mm Tris; 2mm MgCl$_2$ (pH 7.4), and centrifuged at 40,000×g for 10 minutes. The pellet was washed once, resuspended in Tris/MgCl$_2$ and incubated with 8 units/ml adenosine deaminase at 37° C. for 30 minutes. The homogenate was centrifuged, washed once, resuspended to a protein concentration of 5–10 mg/ml and frozen at −70° C. until use. The results in Table 4 below show that the test compound has 170 times more affinity for $A_1$ receptors than for $A_2$ receptors.

TABLE 4

Selectivity of $N^6$-endo-2-Norbornyl-9-MA
Bovine Caudate Binding

| At $A_1$ Receptors $K_i$ (M) | At $A_2$ Receptors $K_i$ (M) |
|---|---|
| $4.1 \times 10^{-8}$M | $6.96 \times 10^{-6}$M |
| | A1/A2 = 5.89 – $10^{-3}$ |
| | = 170 fold selective for $A_1$ receptors |

REFERENCES

Munson, Peter J. and Rodbard, David (1980). "Ligand: A Versatile Computerized Approach for Characterizing Ligand binding Systems." Anal. Biochem. 107:220–239.

Bruns, Robert F., Lee, Gina H., and Pugsley, Thomas A. (1986) "Characterization of the $A_2$ Adenosine Receptor Labeled by $^3$H-NeCA in Rat Striatal Membranes," Mol. Pharmacol. 29:331–346.

These $N^6$-substituted adenines are antagonists of $A_2$adenosine receptor-mediated stimulation of adenylate cyclase in $A_2$-adenosine receptors and antagonists of $A_1$-adenosine receptor-mediated inhibition of adenylate cyclase. These compounds are useful in reversal of adenosine-mediated lipolysis, reversal of adenosine-mediated deleterious cardiovascular effects (conduction defects, hypotension), reversal of adenosine-mediated vascular actions in kidney, bronchodilation, antiarrhythmic action, reversal of adenom-ediated relaxation of smooth muscle, anti-narcoleptic action, CNS stimulation, and blockade of adenosine mediated inhibition of neurotransmitter release.

While not wishing to be bound by theory as to the mechanism of action involved, it has been found that the optically active compounds covered by this invention such as the 1R,2S,4S- and 1S,2R,4R-(endo-2-Norbornyl)-9-methyladenines, especially those substituted with hydrogen and halogen at the 8 position, show greatly increased selectivity as $A_1$ adenosine receptor antagonists over racemic mixtures of the compound. Of the two groups of enantiomers, the 1R,2S,4S Norbornyl compounds show the greatest increase in selectivity for $A_1$ adenosine receptors. The compounds of this invention have been found to be useful in the treatment of glaucoma.

While particular embodiments of the invention have been described it will be understood of course that the invention is not limited thereto since many obvious modifications can be made and it is intended to include within this invention any such modifications as will fall within the scope of the appended claims.

What is claimed is:

1. A compound having the formula:

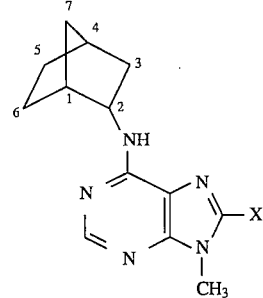

or stereoisomers thereof;
wherein X is hydrogen.

2. A compound of claim 1 wherein said compound is one of:

$N^6$-[endo(1R,2S,4S)-2-norbornyl]-9-methyladenine or
$N^6$-[endo(1S,2R,4R)-2-norbornyl]-9-methyladenine.

* * * * *